*(12)* United States Patent
Röll

(10) Patent No.: US 8,304,231 B2
(45) Date of Patent: Nov. 6, 2012

(54) BIOREACTOR

(75) Inventor: Marcel Röll, Maur (CH)

(73) Assignee: Sartorius Stedim Switzerland AG, Tagelswangen (CH)

( * ) Notice: Subject to any disclaimer, the term of this patent is extended or adjusted under 35 U.S.C. 154(b) by 413 days.

(21) Appl. No.: 11/660,463

(22) PCT Filed: Aug. 10, 2005

(86) PCT No.: PCT/CH2005/000464
§ 371 (c)(1),
(2), (4) Date: Apr. 16, 2007

(87) PCT Pub. No.: WO2006/017951
PCT Pub. Date: Feb. 23, 2006

(65) Prior Publication Data
US 2007/0292940 A1    Dec. 20, 2007

(30) Foreign Application Priority Data
Aug. 16, 2004   (CH) .................................... 1352/04

(51) Int. Cl.
*C12M 1/34*   (2006.01)
*C12M 3/00*   (2006.01)

(52) U.S. Cl. ............... 435/288.7; 435/289.1; 435/287.1; 435/808; 73/863.81; 422/82.05; 422/82.11; 385/12

(58) Field of Classification Search ............... 435/288.7, 435/289.1, 287.1, 808; 73/863.81; 204/433; 422/82.05, 82.11; 385/12
See application file for complete search history.

(56) References Cited

U.S. PATENT DOCUMENTS

| | | | |
|---|---|---|---|
| 4,778,583 A * | 10/1988 | Wagner et al. ........... 204/192.37 |
| 5,124,130 A * | 6/1992 | Costello et al. ............ 422/82.06 |
| 5,164,796 A | 11/1992 | Di Guiseppi et al. |
| 5,888,805 A | 3/1999 | Endo et al. |
| 6,190,913 B1 * | 2/2001 | Singh ............................ 435/394 |
| 6,730,471 B1 | 5/2004 | Katerkamp et al. |
| 2006/0051874 A1 * | 3/2006 | Reed et al. .................... 436/163 |
| 2006/0131765 A1 * | 6/2006 | Terentiev et al. ............... 261/93 |

FOREIGN PATENT DOCUMENTS

| | | |
|---|---|---|
| EP | 0810281 | 12/1997 |
| WO | WO 93/15402 | 8/1993 |
| WO | WO 00/66706 | 11/2000 |

* cited by examiner

*Primary Examiner* — William H Beisner
*Assistant Examiner* — Danielle Henkel
(74) *Attorney, Agent, or Firm* — Lucas & Mercanti, LLP; Klaus P. Stoffel

(57) ABSTRACT

The invention relates to a bioreactor, comprising a reactor vessel (2) with a housing support (20,20*a*), extending into the vessel interior (14), with a medium seal against the vessel interior (14) with a transparent sensor piece (34,34*a*) and an indicator tile (38,38*a*), arranged in the vessel interior (14), in contact with the vessel contents, which may be scanned by a fiber optic which may itself be introduced into the housing support (20,20*a*) and connected to a display device (24). In order that the reactor may be embodied as a bag, the housing support (20,20*a*) is arranged on the upper side of the reactor bag and provided with a flange piece (26) tightly sealed to the vessel wall (28). The flange piece is connected to the sensor piece (34,34*a*) by means of a preferably tubular connector piece (32,23*a*), whereby the length of the connector piece is such that the sensor piece (34,34*a*) permanently reaches into the reactant.

5 Claims, 2 Drawing Sheets

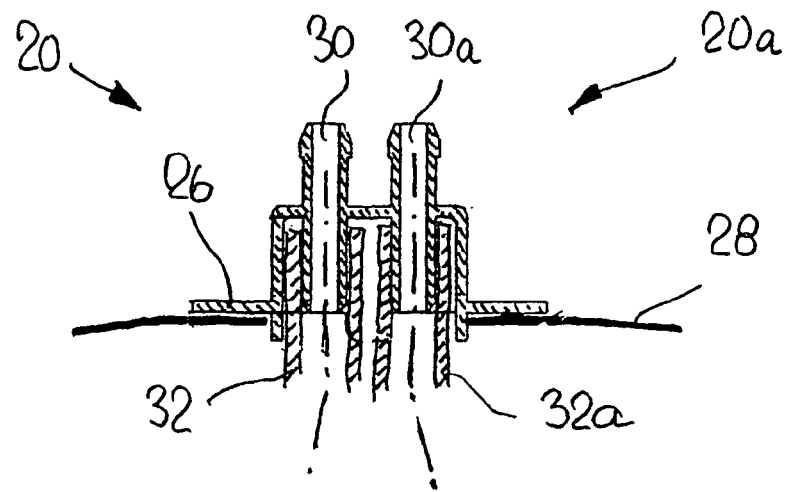
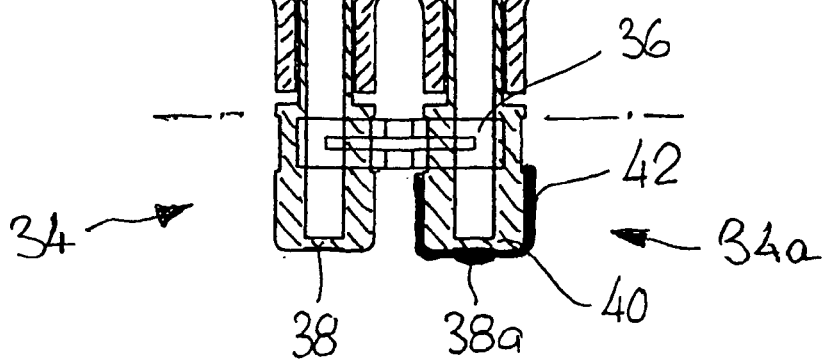
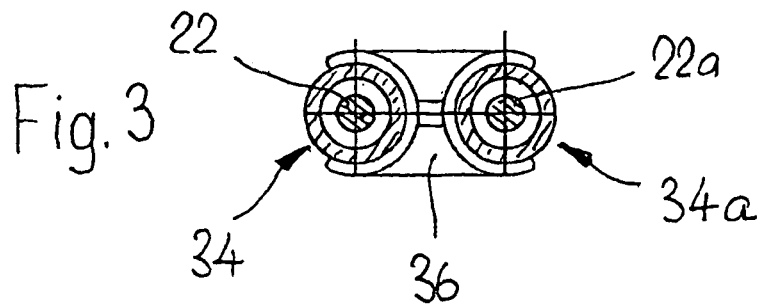
Fig. 2
Fig. 3

BIOREACTOR

This is a National Phase application under 35 U.S.C. 371 of International Application No. PCT/CH2005/000464 filed Aug. 10, 2005, which claims priority of Swiss Application No. 1352/04 filed Aug. 16, 2004.

TECHNICAL FIELD

The present invention relates to a bioreactor.

PRIOR ART

A bioreactor of the above mentioned type is known, for example, from U.S. Pat. No. 6,730,471 B. The reactor vessel comprises at the bottom thereof a port formed thereon extending into the interior of the reactor vessel, the port being provided with a sensor membrane that is in contact with the reactant. A fiber optic that is connected with a display device can be attached to the port. Such a connecting port is not suitable for a bag-shaped reactor, because due to the flexibility of the wall a connecting port cannot be formed on the bag. Moreover, the bag-like reactor has to be supported on a support, so that the lower side is also not suitable for the arrangement of the connecting port. The publication does not provide any information concerning the arrangement of an electro-optical sensor at a reactor designed as a bag.

A reactor vessel designed as a bag is known, for example, from WO 00/66706. This bag-like reactor vessel is provided with connections, one of which, in particular, is also suitable for inserting a sensor for determining properties of the reactant. It is a disadvantage that the connection, on the one hand, and the sensor that is inserted into the vessel interior via the connection, on the other hand, have to be kept sterile. This embodiment always holds the danger that impurities are brought into the reactor vessel and thus into the reactant by the sensor.

DESCRIPTION OF THE INVENTION

It is an object of the invention to improve a bioreactor of the above mentioned type in order to design it as bag.

This object is achieved by a bioreactor having a reactor vessel with a receiving port that extends into the vessel interior in medium-tight fashion against the vessel interior. A transparent sensor piece with an indicator tile is arranged in the vessel interior to be in contact with the vessel contents. The indicator tile may be scanned by a fiber optic that may be introduced into the receiving port and is contacted to a display device. The reactor vessel is embodied as a bag. The receiving port is arranged at the upper side of the reactor bag and is provided with a flange piece tightly sealed to the vessel wall and connected to the sensor piece via a preferably tubular connector piece in such a way that the sensor piece reaches into the reactant from above.

By virtue of the fact that the receiving port is arranged at the upper side of the reactor bag, the lower support surface necessary for a bag is not impaired. The flange piece tightly connected with the vessel wall allows for a secure connection to the flexible wall of the bag. The preferably tubular connector piece establishes the connection with the sensor piece. The length of the connector piece is such that the sensor piece reaches into the reactant from above.

The receiving port comprising the indicator tile can be sterilized together with the interior of the reactor vessel. It is no longer necessary for the fiber optic to undergo a particular sterilization because it does not come into contact with the vessel interior and thus with the reactant.

It is a particular advantage if the receiving port is arranged in the central region of the reactor bag, thus ensuring that the sensor always stays in contact with the reactant even during the oscillating movements usually imparted to the bioreactor during the reaction process.

In order to secure the inserted fiber optic at the receiving port and to align it in respect of the indicator tile it is advantageous if the bioreactor comprises means for securing the inserted fiber optic.

According to another embodiment the transparent sensor piece can comprise an end portion with a bottom, wherein the bottom can be directly formed by the indicator tile. However, it is also possible to incorporate the indicator tile within a cap that encloses the end portion of the sensor piece.

According to a further embodiment the reactor vessel can be provided with an analogous second receiving port that is parallel to the first receiving port and comprises an indicator tile for an insertable fiber optic for determining a further property of the reactant.

The indicator tile is designed in known fashion and changes its optical properties depending on the properties to be determined and concentrations of the value to be determined. Therefore, the light beam emitted from the fiber optic on to the indicator tile is reflected and sent back to the display device in a different way, whereupon the latter analyses the changes of the optical properties of the indicator tile accordingly. For example, the indicator tile can be designed for determining the oxygen content of the reactant. Moreover, the indicator tile can also be designed for determining the pH value of the reactant.

In a particularly preferred bioreactor the reactor bag is made of plastic and can be clamped at two opposite sides thereof to a support. Thereby, another embodiment is advantageous, according to which the insertable sides each comprise a seam which is provided with a bulged rim extending transversally to the clamping direction.

BRIEF DESCRIPTION OF THE DRAWINGS

Examples of the invention will henceforth be described in more detail by reference to the drawings, wherein are shown:

FIG. 2 a connecting port of the bioreactor, in a vertical section and in larger scale;

FIG. 3 the sensor piece of the connecting port according to FIG. 2, along the section III-III.

MODES FOR CARRYING OUT THE INVENTION

Figure 1:
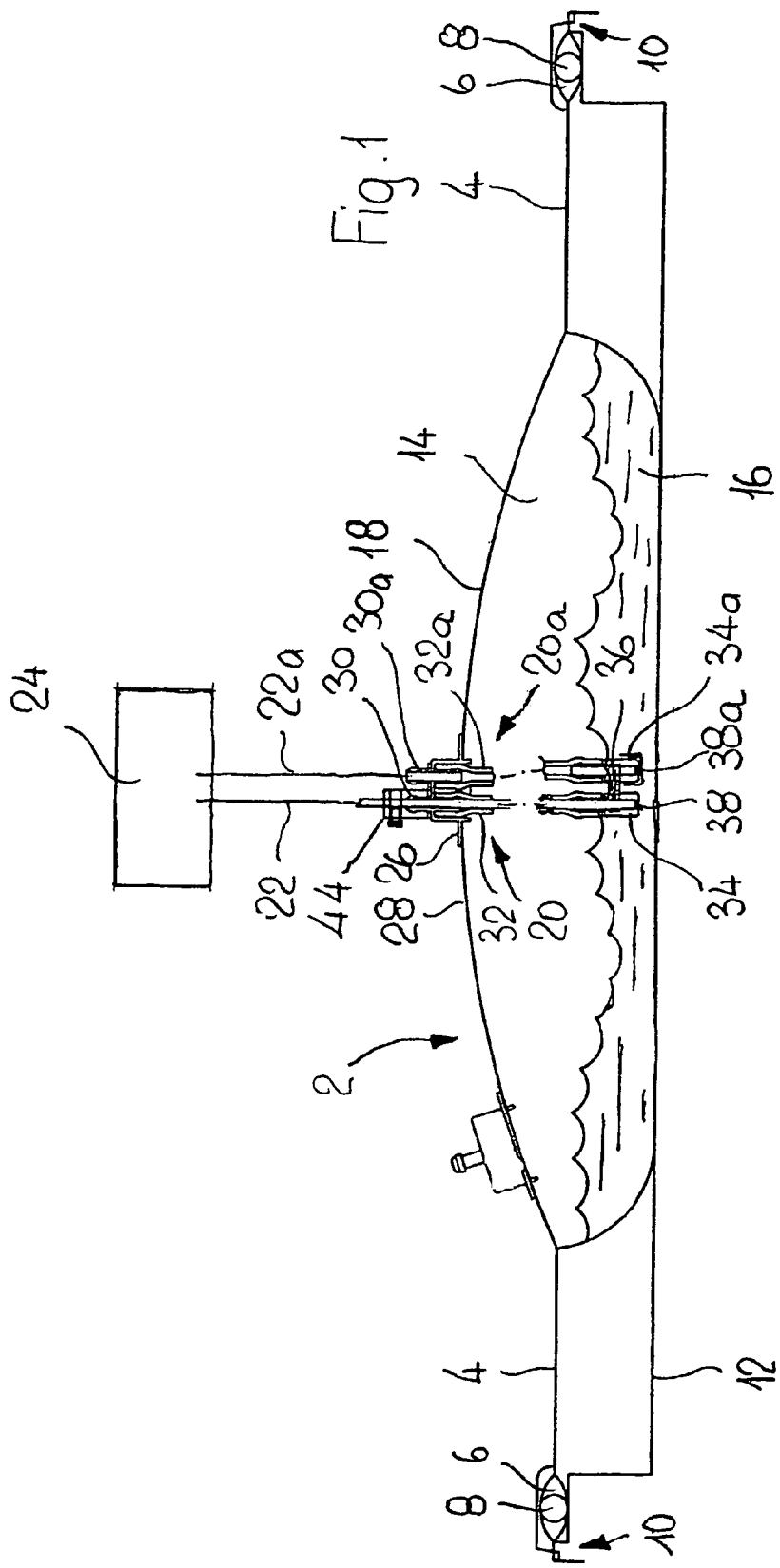
FIG. 1 a bioreactor, in a vertical section.

FIG. 1 shows a bioreactor with a reactor bag 2 that comprises at two opposite sides 4 thereof a seam 6 which is provided with a bulged rim 8. The seam 6 provided with the bulged rim 8 is clamped in a clamping device 10 of a support 12 for the reactor bag.

The interior 14 of the reactor bag 2 serves for receiving a reactant 16 that, for example, can be a biological material. A receiving port 20 that is shown here in a twin arrangement, is arranged at the upper side 18 of the reactor bag 2 and extends into the interior 14 of the reactor bag so as to reach the reactant 16. In each one of the two receiving ports 20, 20a there is inserted a fiber optic 22, 22a that is directed to the display device 24 in order to analyze the reaction signals of the fiber optic and to determine certain properties of the reactant.

The receiving ports 20, 20a are shown in FIGS. 2 and 3 in more detail. They comprise a flange piece 26 that is connected medium-tightly connected with the wall 28 of the reactor bag 2. The flange piece 26 comprises pipe ports 30, 30a that are connected at the interior 14 of the reactor bag 2 with tubular connector pieces that lead to transparent sensor pieces 34, 34a to which they are also medium-tightly connected. The sensor pieces 34, 34a are held together via a clamp 36. The sensor piece 34 comprises at the bottom thereof a potted-in or glued-on indicator tile 38 that is in contact with the interior 14 of the reactor bag 2 and thus also with the reactant 16. The sensor piece 34a can be designed analogously to the sensor piece 34; in the present example, however, the indicator tile 38a is not arranged at the bottom 40 of the sensor piece 34 but in a cap 42 that encloses the sensor piece. The bottom 40 is designed transparently so that the optical properties of the indicator tile 38a can be monitored through the bottom 40 of the fiber optic 22, 22a. The receiving port 20, 20a with its connector piece 32, 32a and the sensor piece 34, 34a is designed medium-tight against the interior 14 of the reactor bag 2, so that the portion of the receiving port located in the interior of the reactor vessel can be sterilized together with the reactor bag upon manufacturing or on-site. In respect of the fiber optic 22, 22a, a sterilization is no longer necessary as it can be inserted into the receiving port 20, 20a on-site when needed without extensive manipulations. A securing member 44 for the fiber optic 22 as shown is provided for securing the fiber optic 22, 22a in the receiving port 20, 20a and for its alignment in respect of the indicator tile 38, 38a. The light beams emitted from the display device 24 are then refracted at the indicator tile 38, 38a, whereupon the reflected beams are sent back to the display device 24 where they are analyzed. Depending on the indicator tile 38, 38a being applied, various values of the reactant such as, for example, the oxygen content or the pH value can be determined and kept in the corresponding range.

The reactor bags come in various sizes so that the distance of the upper wall from the bottom of the reactor bag can vary accordingly. The length of the connector piece between the connecting port and the sensor piece can always be chosen in such a way that the sensor piece is immersed into in the reactant.

The invention claimed is:

1. A bioreactor, comprising a reactor vessel (2) with a receiving port (20, 20a) that extends into an interior (14) of the vessel in medium-tight fashion against the vessel interior (14), comprising a transparent sensor piece (34, 34a) with an indicator tile (38, 38a) arranged in the vessel interior (14) in contact with contents of the vessel, which indicator tile may be scanned by a fiber optic that may be introduced into the receiving port (20, 20a) and is contacted to a display device (24), wherein the reactor vessel is embodied as a bag, wherein the receiving port (20, 20a) is arranged at an upper side of the reactor bag and is provided with a flange piece (26) tightly sealed to the vessel wall (28), the receiving port including means for securing the inserted fiber optic and the receiving port being connected to the sensor piece (34, 34a) via a tubular connector piece (32, 23a) in such a way that the sensor piece (34, 34a) reaches into the reactant from above, wherein the sensor piece (34, 34a) comprises an end portion with a bottom (40), wherein the bottom (40) is incorporated within a cap (42) that encloses the end portion, and wherein the reactor bag can be clamped at two opposite sides (4) thereof to a support (12), wherein the receiving port (20, 20a) is arranged in a central region of the reactor bag, ensuring that the sensor is always in contact with the reactant even during oscillating movements imparted to the bioreactor during a reaction process, the bioreactor further comprising an analogous second receiving port (20a) that is parallel to the first receiving port (20) and comprises an indicator tile (38a) for an insertable fiber optic (22a) for determining a further property of the react an wherein a second sensor piece is connected to the second receiving port, and further comprising a clamp that holds the sensor pieces together in parallel.

2. The bioreactor according to claim 1, wherein the receiving port (20, 20a) comprises means (44) for securing the inserted fiber optic (22, 22a).

3. The bioreactor according to claim 1, wherein the indicator tile (38) is designed for determining oxygen content of the reactant (16).

4. The bioreactor according to claim 1, wherein the indicator tile (38a) is designed for determining the pH value of the reactant (16).

5. The bioreactor according to claim 1, wherein sides (4) which can be clamped each comprise a seam (6) which is provided with a bulged rim (8) extending transversally to a clamping direction.

* * * * *